United States Patent [19]

Dubowik

[11] Patent Number: 4,665,604

[45] Date of Patent: May 19, 1987

[54] NON-FUSED TORQUE CONTROL CATHETER

[75] Inventor: John M. Dubowik, Nashua, N.H.

[73] Assignee: Cordis Corporation, Miami, Fla.

[21] Appl. No.: 348,862

[22] Filed: Feb. 16, 1982

[51] Int. Cl.$^4$ .............................................. B23P 17/00
[52] U.S. Cl. ..................................... 29/415; 604/282;
264/150; 264/174; 156/143; 87/1; 87/9; 87/11; 138/125
[58] Field of Search ................ 604/282; 138/125, 123, 138/127; 87/1, 6, 7, 9, 11; 156/143; 29/415, 402, 451, 525; 264/103, 150, 174

[56] References Cited

U.S. PATENT DOCUMENTS

| | | | |
|---|---|---|---|
| 2,472,483 | 6/1949 | Krippendorf | 604/282 X |
| 3,249,666 | 5/1966 | French | 138/127 X |
| 3,416,531 | 12/1968 | Edwards | 604/282 X |
| 3,485,234 | 12/1969 | Stevens | 128/2 |
| 3,498,286 | 3/1970 | Polanyi et al. | 604/282 X |
| 3,585,707 | 6/1971 | Stevens | 29/427 |
| 3,965,909 | 6/1976 | Waddell et al. | |

FOREIGN PATENT DOCUMENTS 2043201 11/1980 United Kingdom .

Primary Examiner—Stephen C. Pellegrino
Attorney, Agent, or Firm—George H. Gerstman; Henry W. Collins

[57] ABSTRACT

Disclosed is a non-fused torque control catheter and a method for manufacturing such a catheter. This non-fused catheter has a stiff braid-reinforced body and a pliable non-braided tip.

12 Claims, 6 Drawing Figures

NON-FUSED TORQUE CONTROL CATHETER

BACKGROUND OF THE INVENTION

The invention relates to a non-fused torque control catheter, and a method for making such a catheter. More particularly, this invention relates to a catheter with a stiff braid reinforced body which is molded with its pliable nonbraided tip intact.

The main use of torque control catheters is for angiographic testing. Very often subtle maneuvering of the catheter must be performed in order to locate precisely the catheter at its desired location. This requires that considerable torque control be exercised over the catheter, thus the body of the catheter is braid reinforced. It is not desirable though, that this stiffness exist at the distal end of the catheter which may make direct contact with the heart (or other bodily organ being investigated). The distal end of the catheter must remain pliable and resilient in order to work its way into confined areas within the organ without causing damage thereto.

Previously, a torque controlled braided catheter body and a non-braided pliable tip were fabricated separately and then joined together by a thermal bond, a solvent bond, an adhesive or any other suitable method. The internal lumen of the braided catheter and the non-braided pliable tip were aligned and interconnected to allow communication therebetween.

Many problems exist when the body of the catheter and the tip of the catheter are fabricated separately and then joined together. In the joint area, there is a good likelihood of an exposed braid wire in the lumen or at the finished surface. It is also quite difficult to exactly align the tip lumen and the body lumen, thus there may be interference with the passage of the guide wire. Furthermore, there is always the possibility of a fuse failure during use.

Accordingly, it is an object of the present invention to provide a non-fused torque control catheter with a pliable tip.

It is a further object of the present invention to fabricate such a catheter in an efficient, reliable and inexpensive manner.

SUMMARY OF THE INVENTION

The problems of the prior art are overcome by the instant invention which comprises a non-fused torque control catheter and a method for manufacturing such a catheter. The non-fused catheter has a stiff, braid-reinforced body and a pliable non-braided tip. Manufacture of catheters is begun by extruding a suitable plastic onto a ductile wire mandril by conventional wire coating extrusion apparatus to form a catheter base coat. Next, the continuous strand of catheter base coat undergoes a braiding operation. Then the braid is embedded to the base coat in areas that will form the bodies of the catheters by passing the base coat through a heated die. In the areas of the base coat that will form the tips of catheters, the braid is not heat embedded, but is rather allowed to lie loosely on the surface of the plastic base coat. The exposed wire in this tip area is then electrochemically removed. A second extruded layer of plastic is applied to the continuous strand of base coat in order to bring the continuous strand to final dimension for forming catheters.

The continuous strand is then cut to length and the wire mandril is removed. The catheter is then completed by finishing the tip, and attaching a conventional needle hub fitting to the proximal end.

DESCRIPTION OF THE PREFERRED EMBODIMENT

Figure 1:
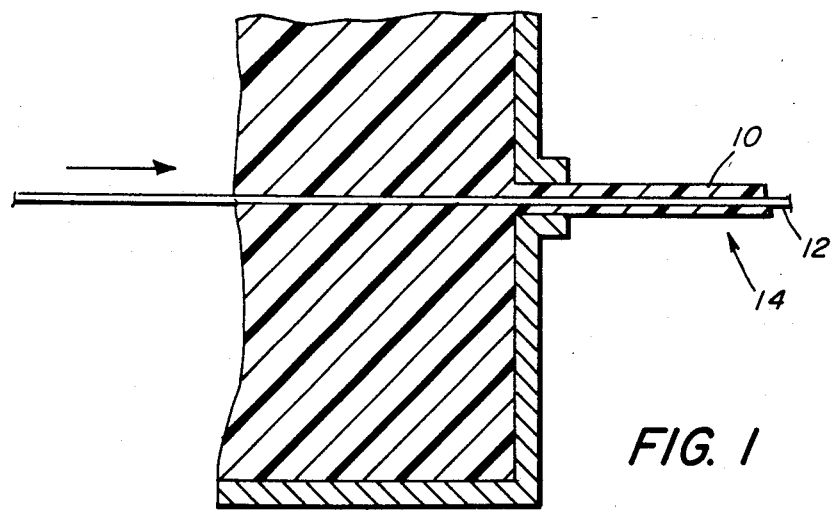
FIG. 1 is a side view of an extrusion of semi-soft plastic elastomeric material onto a silver-coated copper wire.

As seen in FIG. 1, the first step in the formation of a continuous strand of catheter is to extrude a semi-soft plastic elastomeric material 10 onto a silver-coated copper wire 12 to form a base strand 14. Typically, conventional extrusion apparatus of the type used to apply plastic insulation to electrical wire is employed, with an elastomeric polyurethane resin as the covering material.

Figure 2:
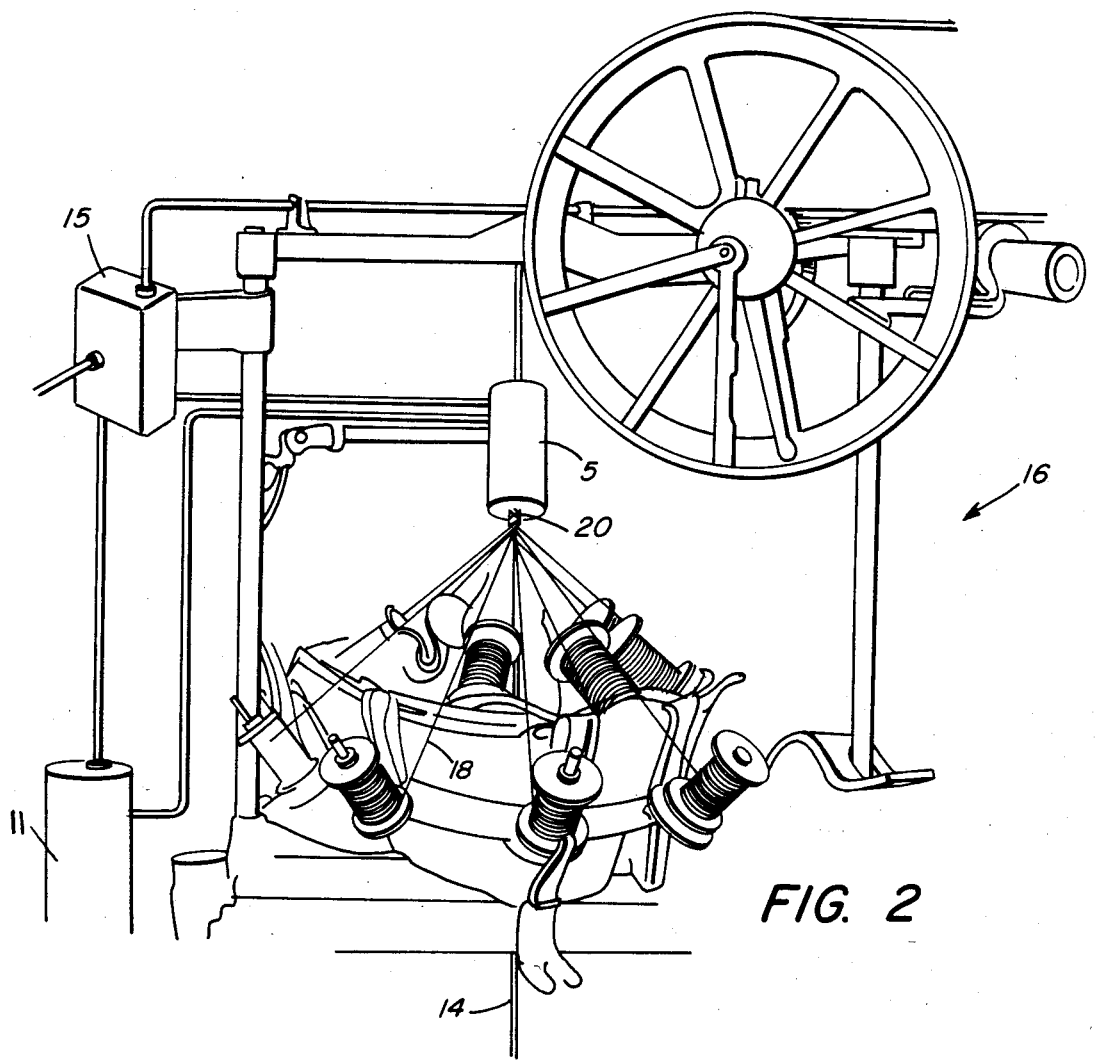
FIG. 2 is a perspective view of a braid staking machine modified in accordance with the present invention to use heat in order to embed the braid to the plastic base strand.
Figure 3:
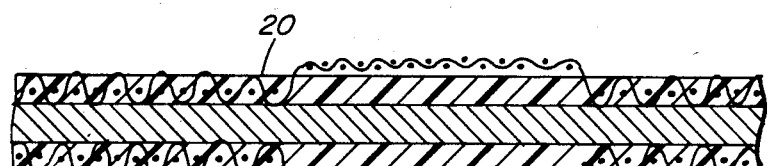
FIG. 3 is a cross sectional view of a base strand with braid wire embedded to the base strand in the body region and braid wire lying loosely on the surface of the base strand in the tip region.

After the first extrusion, the base strand 14 is run through a braid staking machine 16 as is shown in FIG. 2. First, the catheter base strand 14 is fully braided with 304 stainless steel wire 18 to form a braid 20 over strand 14. Then sections of the braid 20, located in what will be the braid reinforced body areas of the catheters, are embedded to the coating on strand 14. The braid can be embedded into the coating beneath the coating, or flush with the surface of the coating. Sections of the braid 20, located in what will be the tip areas of the catheter are allowed to lie loosely on the surface of the plastic base coat as is shown in FIG. 3. The braid 20 is embedded by passing the base strand 14 through a heated dye 5 at a temperature sufficient to embed the strand 20. When the part of the base strand that will become the tip of the catheter is reached, the dye 5 is chilled by a fluid chiller 11, causing the braid 20 to lie loosely on the surface of the base strand 14, rather than be embedded. A die temperature controller 15 regulates the temperature of the die. The rapid heating and cooling characteristics of the low thermal mass die, controlled automatically and cycled by the braider draw system, provide accurate and consistent on-off braid staking with easy adjustability for different catheter styles.

A preferred alternate approach to fully braiding the catheter base strand would be to only braid sections of the base strand located in what will be the body regions of the catheters and to leave straight wire lying loosely on the surface in the sections of the base strand that will form the tip regions of the catheter. This would be accomplished by turning off the braiding machine when the part of the base strand that will become the tip of the catheter is reached. The same heat embedding procedure used for the fully braided catheter base strand would then be followed.

Figure 4:
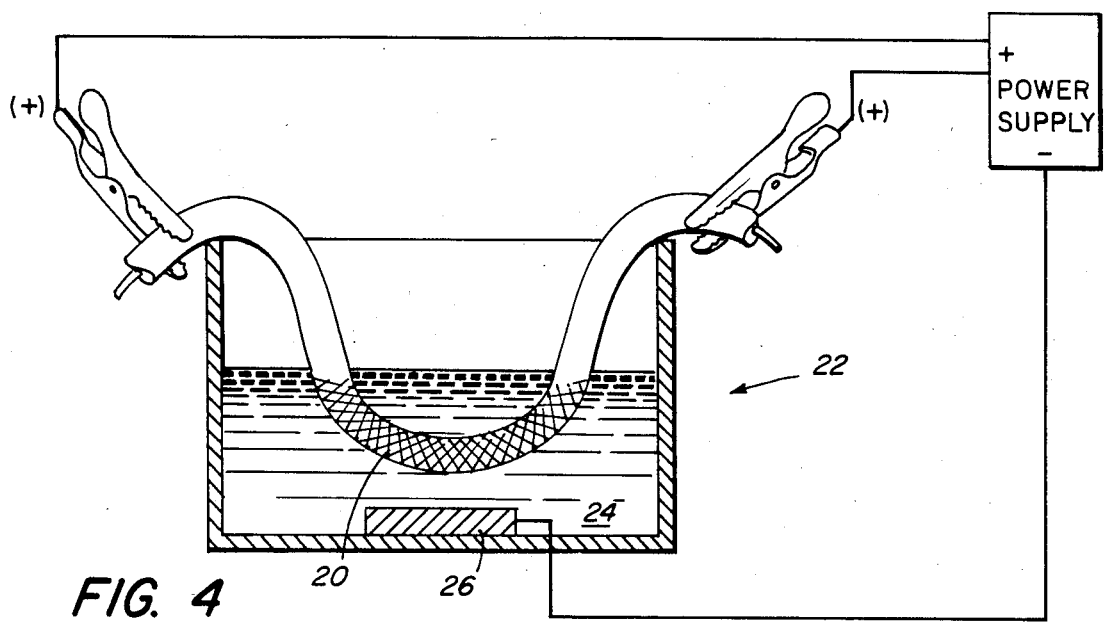
FIG. 4 is a side view of a braided base strand undergoing electrochemical removal of the braid wire lying loosely on the surface of the base strand in the tip region.

As shown in FIG. 4, the braid 20, lying loosely in what will be the tip region of the finished catheter, is then electrochemically removed. If the above-described alternate approach is followed, straight wire, rather than braid, will be electrochemically removed. In order to remove the braid 20 from the tip region, the tip region is exposed to a saturated salt water bath 24. This saturated saline solution serves as the electrolyte in the electrochemical metal removal process. The bath is agitated because turbulence enhances cleanliness in the removal area. Alligator clips 27 attached to the catheter base strand connect the braid 20 to the positive terminal of a power supply. Any kind of clip that can penetrate the base coat 10 and make electrical contact with braid 20 can be used. A piece of copper 26 in the bath serves as the counter-electrode for the process. This piece of copper is connected to the negative terminal of a power supply. Other metals besides copper, such as bronze, can be employed in the process. The amount of electric current used is approximately 1.5 amps. It takes about 10 minutes to electrochemically remove the braid from what will be one catheter length. The stainless steel 18 flows from the braid 20 to the electrode 24. The stainless steel does not reach the electrode, but instead gets washed away as metallic salt.

Figure 5:
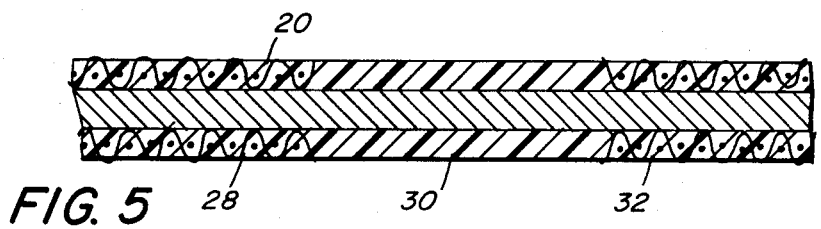
FIG. 5 is a cross sectional view of a catheter base strand with embedded braid in the body area and no braid in the tip area.

What remains after the electrochemical removal process is a continuous strand of base coat as seen in FIG. 5 with alternating braid-reinforced sections 28 and non braid reinforced sections 30. A final extrusion of semi-soft plastic elastomeric material is then applied in order to bring the catheter base strand to final dimension.

Figure 6:
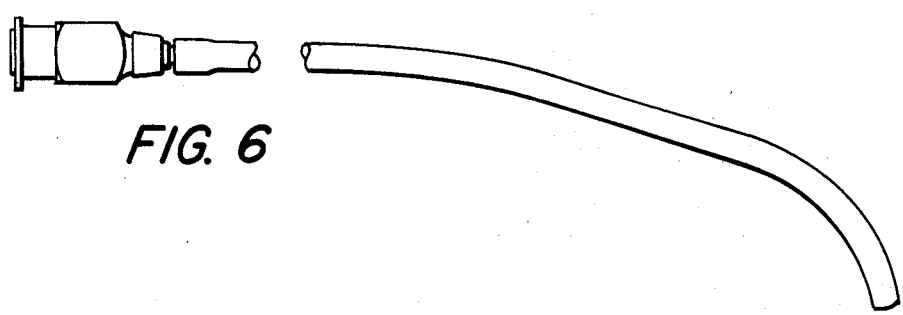
FIG. 6 is a side view of a finished catheter of the invention.

The continuous strand of FIG. 5 is cut to catheter lengths at the intersections 32 of the body and the tip sections and the silver-plated copper wire is stretched to reduce its diameter and enable removal. As is seen in FIG. 6, the catheter is then completed by finishing the tip and attaching a proximal fitting which may by a conventional female needle Luer Lok type fitting attached in conventional manner.

The invention is further illustrated by the following non-limiting example:

EXAMPLE I

An elastomeric polyurethane, Ducor, manufactured by Cordis Corporation is extruded onto a silver-coated copper wire to form a catheter base strand. Conventional extrusion apparatus of the type used to apply plastic insulation to electrical wire is employed. The base strand is run through a Wardwell braiding machine, modified to include a heating process for embedding braid to a catheter base strand. First, the base strand is fully braided with 304 stainless steel wire. Then sections of the braid, located in what will be the braid-reinforced body areas of the based strand are embedded to the base strand by passing the base strand through a sizing die heated to 350° F. The dimensions of the die are such that both ends of the sizing die are larger than the catheter base strand and the middle of the sizing die is the same size as the catheter base strand. When the part of the base strand that will become the tip of the catheter is reached, the dye is chilled to room temperature by a fluid chiller, causing the braid to lie loosely on the surface of the base strand, rather than be embedded. The braid lying loosely on the surface of the base strand is exposed to a turbulent saline bath containing approximately one pound of NaCl per gallon of $H_2O$. Alligator clips attached to the catheter base strand connect the braid to the positive terminal of a power supply. A piece of copper in the bath is connected to the negative terminal of the power supply. The electric current used is approximately 1.5 amps or about 10 volts. After the electrochemical removal process, a final extrusion of "Ducor" is applied to bring the catheter base strand to final dimension.

The continuous base strand is cut to desired catheter length, usually between 55 and 120 centimeters, and the silverplated copper wire is stretched to reduce its diameter and is removed. The catheter is completed by grinding, shaping and punching of the tip and attaching in conventional manner a female needle Luer Lok type fitting.

I claim:

1. A continuous strand of braided catheter basecoat wherein the braid is embedded to the base strand in what will be the body area of the catheter and left unembedded in the tip area of the catheter, where it is to be removed.

2. The braided catheter base strand of claim 1 wherein said braid is embedded to the base strand in what will be the body area of the catheter by passing said base strand through a heated die at a temperature sufficient to embed the braid.

3. The braided catheter base strand of claim 1 wherein said braid is left unembedded in what will be the tip area of the catheter by chilling the die through which the braided base strand is passed.

4. A continuous strand of catheter basecoat, braided in the sections that will form the body areas of the catheters, and having straight wire lying loosely on the surface of the section that will form the tip areas of the catheters wherein the braid in the body areas is embedded to the base strand and the straight wire in the tip areas is left unembedded.

5. The catheter base strand of claim 4 wherein said braid is embedded to the base strand in what will be the body areas of the catheters by passing said base strand through a heated die at a temperature sufficient to embed the braid.

6. The catheter base strand of claim 4 wherein said straight wire is left unembedded in what will be the tip areas of the catheters by chilling the die through which the braided base strand is passed.

7. A process for making a non-fused torque control catheter comprising the steps of:
   (a) extruding a suitable plastic onto a ductile wire mandrel, by conventional wire coating extrusion apparatus;
   (b) braiding the base strand of (a) with wire;
   (c) embedding the braid to the base strand of what will be the body areas of the finished catheters and leaving the braid unembedded in what will be the tip areas of the finished catheters;
   (d) removing the braid in what will be the tip areas of the finished catheters by electrochemical metal removal;
   (e) applying a final extrusion of a suitable plastic to the continuous strand of catheter in order to bring the catheter strand to final dimension;
   (f) cutting the continuous strand of catheter to catheter lengths and removing the wire mandril;
   (g) finishing the tip and attaching a conventional needle hub fitting to the proximal end.

8. The process as set forth in claim 7 wherein in claim 7, step C the braid is embedded to the base strand in what will be the body areas of the finished catheters by passing the base strand covered with braid through a heated die at a temperature sufficient to embed the braid.

9. The process as set forth in claim 7 wherein in claim 7, step C the braid is left unembedded in the tip areas of the catheters by chilling the die through which the base strand covered with braid is passed.

10. A process for making a non-fused torque control catheter comprising the steps of:
 (a) extruding a suitable plastic onto a ductile wire mandrel, by conventional wire coating extrusion apparatus;
 (b) braiding sections of the base strand of (a) located in what will be the body areas of the catheters with wire and leaving straight wire lying loosely on the surface in the sections of the base strand of (a) that will form the tip areas of the catheters;
 (c) embedding the braid to the base strand in what will be the body areas of the finished catheters and leaving the straight wire unembedded in what will be the tip areas of the finished catheters;
 (d) removing the straight wire in what will be the tip areas of the finished catheters by electrochemical metal removal;
 (e) applying a final extrusion of a suitable plastic to the continuous strand of catheter in order to bring the catheter strand to final dimension;
 (f) cutting the continuous strand of catheter to catheter lengths and removing the wire mandril;
 (g) finishing the tip and attaching a conventional needle hub fitting to the proximal end.

11. The process as set forth in claim 11 wherein in claim 10, step (c), the braid is embedded to the base strand in what will be the body areas of the finished catheters by passing the base strand covered with braid through a heated die at a temperature sufficient to embed the braid.

12. The process as set forth in claim 10 wherein in claim 10, step (c), the straight wire is left unembedded in the tip areas of the catheters by chilling the die through which the base strand is passed.

* * * * *

UNITED STATES PATENT AND TRADEMARK OFFICE
CERTIFICATE OF CORRECTION

PATENT NO.   : 4,665,604

DATED        : May 19, 1987

INVENTOR(S)  : John M. Dubowik

It is certified that error appears in the above-identified patent and that said Letters Patent is hereby corrected as shown below:

Column 6, line 13, change "11" (second occurrence) to
- - 10 - -.

Signed and Sealed this

Twentieth Day of October, 1987

Attest:

DONALD J. QUIGG

Attesting Officer

Commissioner of Patents and Trademarks